United States Patent [19]

Altuglu

[11] 4,273,726
[45] Jun. 16, 1981

[54] POLYOL (ALLYL CARBONATE) SYNTHESIS UTILIZING SOLID ALKALI METAL HYDROXIDE

[75] Inventor: Senol Altuglu, Doylestown, Ohio

[73] Assignee: PPG Industries, Inc., Pittsburgh, Pa.

[21] Appl. No.: 93,424

[22] Filed: Nov. 13, 1979

[51] Int. Cl.³ .............................................. C07C 68/02
[52] U.S. Cl. ................................................... 260/463
[58] Field of Search ........................................ 260/463

[56] References Cited

U.S. PATENT DOCUMENTS

| | | | |
|---|---|---|---|
| 2,370,571 | 2/1945 | Muskat et al. | 260/463 |
| 2,384,125 | 9/1945 | Muskat et al. | 260/463 |
| 2,455,653 | 12/1948 | Bralley et al. | 260/463 |
| 3,530,094 | 9/1970 | Schnell et al. | 260/463 |

Primary Examiner—Donald G. Daus
Assistant Examiner—M. C. Eakin
Attorney, Agent, or Firm—Richard M. Goldman

[57] ABSTRACT

Disclosed is a method of synthesizing a polyol (allyl carbonate) by the alkali metal hydroxide catalyzed reaction of allyl alcohol and a polyol chloroformate where a portion of the alkali metal hydroxide is anhydrous.

2 Claims, No Drawings

POLYOL (ALLYL CARBONATE) SYNTHESIS UTILIZING SOLID ALKALI METAL HYDROXIDE

This invention relates to the synthesis of bis (allyl carbonate) monomers. Bis (allyl carbonate) monomers find utility in the formation of optical polymers, for example, for lenses, as glazing materials, and as tough transparent articles.

Typically, bis allyl carbonate monomers have been synthesized by reacting a bis chloroformate with allyl alcohol in the presence of aqueous alkali metal hydroxide, for example, aqueous sodium hydroxide or aqueous potassium hydroxide. Most commonly the aqueous alkali metal hydroxide has been sodium hydroxide, and the sodium hydroxide has been added to the reaction composition of bis chloroformate and allyl alcohol as a 50 weight percent or less aqueous solution of the aqueous sodium hydroxide.

It has now been found that where the water loading of the alkali metal hydroxide is reduced below about 50 percent, basis total water and alkali metal hydroxide added to the reaction composition, as for example by using more concentrated aqueous sodium hydroxide, or by substituting anhydrous sodium hydroxide for some of the aqueous sodium hydroxide, a higher yield of bis (allyl carbonate) monomer is attained in a shorter reaction time.

DETAILED DESCRIPTION OF THE INVENTION

Bis allyl carbonates are formed by the reaction of bis chloroformate with allyl alcohol in the presence of a Lewis base according to the reaction:

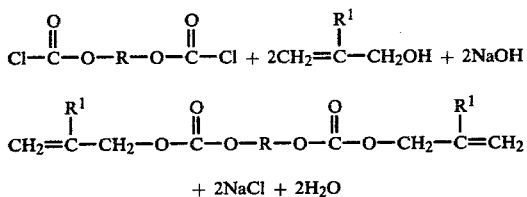

$$+ \ 2NaCl + 2H_2O$$

where R is a diol. Specific examples of R include alkylene groups such as ethylene, trimethylene, methylethylene, tetramethylene, ethylethylene, pentamethylene, hexamethylene, 2-methylhexamethylene, octamethylene, and decamethylene groups, alkylene ether groups such as —$CH_2$—O—$CH_2$—, —$CH_2CH_2$—O—$CH_2CH_2CH_2$—O $CH_2CH_2CH_2$—, and alkylene polyether groups such as —$CH_2CH_2$O—$CH_2CH_2$—O—$CH_2CH_2$—, and —$CH_2$—O $CH_2CH_2$—O—$CH_2$— groups.

The allyl alcohol is represented by the formula:

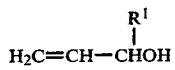

wherein $R^1$ is hydrogen, halogen, or a 1 to 4 carbon group. Specific examples of the allyl alcohol include allyl, 2-chlorallyl, 2-bromoallyl, 2-iodallyl, 2-fluoroallyl, 2-methallyl, 2-ethylallyl, 2-isopropylallyl, 2-n-propylallyl, and 2-n-butylallyl alcohols. Such compounds and methods for making them are disclosed in U.S. Pat. Nos. 2,370,567 and 2,403,113.

The monomers produced by the method of this invention include ethylene glycol bis(2-chloroallyl carbonate), diethylene glycol bis(2-methallyl carbonate), triethylene glycol bis(allyl carbonate) propylene glycol bis(2-ethylallyl carbonate), 1,3-propanediol bis(allyl carbonate), 1,3-butanediol bis (allyl carbonate), 1,4-butanediol(2-bromoallyl carbonate), dipropylene glycol bis(allyl carbonate), trimethylene glycol bis(2-ethylallyl carbonate), and pentamethylene glycol bis(allyl carbonate).

Especially preferred is diethylene glycol bis (allyl carbonate).

The monomers described above are typically synthesized by the reaction of the bis chloroformate with allyl alcohol in the presence of aqueous sodium hydroxide.

In the commercial manufacture of bis allyl carbonates, substantial excess of caustic soda and allyl alcohol are used, giving a bis allyl carbonate yield of approximately 80 to 84 percent basis chloroformate. The caustic soda is used in excess of up to about 30 percent, while the allyl alcohol is used in excess of up to about 30 weight percent. In carrying out the process according to the method of the prior art, a reaction composition of bis chloroformate and approximately 20 to 30 percent excess of allyl alcohol is prepared, and slowly stirred or agitated at a temperature of about 5° to about 15° C. Thereafter, caustic soda of 50 percent or less strength is added slowly. The caustic soda e.g., at 50 weight percent or lower strength is added at a rate slow enough to maintain the temperature of the reaction composition relatively constant. The amount of caustic soda added is an excess of about 15 to about 30 percent. In commercial scale process caustic soda addition may take up to about 90 minutes, while in a laboratory scale or bench scale process caustic soda addition may take 20 to 60 minutes, thereby maintaining the temperature constant, that is a temperature rise of less than about 5° C. over the course of caustic soda addition. Thereafter, the reaction composition is stirred for about 5 minutes to about 1 hour, separated into aqueous and organic phases, and the organic phase washed and settled whereby to recover a crude bis allyl carbonate and toppings. The toppings may be returned to the bis allyl carbonate synthesis process or to a subsequent bis allyl carbonate synthesis process where they constitute about 5 to about 15 percent of the total organic feed to the process.

According to the method herein contemplated, the sodium hydroxide is more than 50 weight percent, anhydrous basis, of the total water and sodium hydroxide, expressed as the quotient $$\frac{\text{Aqueous NaOH (anhydrous basis)} + \text{Anhydrous NaOH}}{\text{Aqueous NaOH (total)} + \text{Anhydrous NaOH}}$$

initially fed to the reaction but preferably less than 61 percent. The yield of bis(allyl carbonate), basis bis(chloroformate) feed, increases and reaction time decreases up to a sodium hydroxide addition of about 61 percent sodium hydroxide, basis total sodium hydroxide and water fed to the reaction. Where the sodium hydroxide is above 61 weight percent, anhydrous basis, of the total water and sodium hydroxide initially fed to the reaction the yield is not increased significantly and the reaction time may be increased because of the lesser amount of water to take up the heat of reaction.

According to a particularly preferred exemplification of this reaction, the sodium hydroxide, anhydrous basis, is from about 54 to about 61 weight percent of the total water and sodium hydroxide initially fed to the reaction and preferably from about 56 to about 59 weight percent of the total water and sodium hydroxide initially fed to the reaction.

As herein contemplated, a portion of the aqueous sodium hydroxide, for example, a portion of the 50 weight percent or 44 weight percent or even 30 weight percent sodium hydroxide may have solid, that is, substantially anhydrous or even anhydrous sodium hydroxide substituted therefor whereby the sodium hydroxide, anhydrous basis, is 54 to 61 weight percent of the total sodium hydroxide and water fed to the reaction medium. For example, where the feed of liquid sodium hydroxide to the reaction composition is 50 weight percent aqueous sodium hydroxide, about 15 to about 35 percent of the sodium hydroxide, anhydrous basis, may be solid sodium hydroxide, and the balance of the sodium hydroxide may be aqueous sodium hydroxide.

The bis allyl carbonate produced by the method of this invention exhibits properties equal to or superior to those of bis allyl carbonates produced where substantially all of the sodium hydroxide is added as aqueous sodium hydroxide of concentration 50 weight percent or lower. For example, the monomer has an opacity approximately equal to or slightly lower than that of the opacity of conventionally produced monomer, the yellowness is approximately equal to or slightly lower than that of conventionally produced monomer, the entrained water is approximately equal to that of the conventionally produced monomer, the viscosity is slightly lower, chloroformate chloride is slightly lower, and the volatile content is slightly lower. Additionally, the yield of allyl carbonate monomer produced according to the method herein contemplated is higher, for example, from about 2 to about 5 percent higher than the yield of allyl carbonate monomer produced where substantially all of the sodium hydroxide is aqueous sodium hydroxide of less than 50 weight percent concentration.

Additionally, the polymer polymerized from the monomer produced by the method of this invention has a light transmission approximately equal to that of the polymerizate of conventionally produced monomer, a lower yellowness, an approximately equal Bar-col Hardness and approximately equal haze.

The exact form of the solid substantially anhydrous or anhydrous caustic soda useful in carrying out the method of this invention may be electrolytic pellets, prilled pellets, flakes or the like. Prills that is prilled pellets, are especially desirable because of their small size and high area per unit mass, thereby providing high reactivity and allowing particularly high loadings of solid caustic as percent of total caustic, for example above 35 percent and even 50 percent total of the total caustic, and anhydrous basis providing for a rapid solution into the reaction composition.

The following examples are illustrative of the method of this invention.

EXAMPLE I

A series of standardization tests approximating commercial practice were conducted. In each test 464.4 grams of diethylene glycol bis (chloroformate), 282.5 grams of allyl alcohol, and 70.6 grams of toppings were mixed in a two liter, four neck, bottled, round bottom flask. The toppings had a nominal composition of 80 to 90 percent diallyl carbonate, 3 to 5 percent allyl alcohol, 4 to 12 percent diethylene glycol bis (allyl carbonate), and water. The allyl alcohol was in 21.6 percent excess.

The flask was immersed in an ice-salt water bath and agitated while 50 weight percent aqueous caustic soda was added to the reaction composition. Three hundred eighty-three and one-half grams of caustic soda were added over a period of 68 minutes, a 20 percent excess. This rate of addition maintained the temperature at 10 to 12 degrees Centigrade.

Thereafter the reaction composition was aggitated at 1 to 5 degrees Centigrade for 30 minutes, and then 500 milliliters of distilled water at 4 to 6 degrees Centigrade was added to the reaction composition, followed by an additional five minutes of stirring.

The organic and aqueous phases were then separated. The results for the four runs are given in Table I.

TABLE I

| | Standardization Runs | |
|---|---|---|
| Run | Yield | Percent Chloroformate Chloride |
| I-A | 86.8 | 0.001 |
| I-B | 87.0 | 0.001 |
| I-C | 87.8 | 0.001 |
| I-D | 87.5 | 0.001 |
| Average yield | 87.3 percent | |
| 95 percent confidence interval | 86.7 to 87.9 percent | |
| 99 percent confidence interval | 86.1 to 88.5 percent. | |

EXAMPLE II–IV

A series of tests were conducted to determined the effect of replacement of part of the aqueous sodium hydroxide with anhydrous sodium hydroxide.

In each test 348.0 grams of diethylene glycol bis (chloroformate), 211.9 grams of allyl alcohol, and 40.0 grams of toppings were mixed as described in Example I above.

The flask was then immersed in an ice-salt water bath and agitated while the sodium hydroxide was added to the reaction composition. In each test 136.4 grams of sodium hydroxide, anhydrous basis, was added to the reaction composition. In each test one half of the aqueous sodium hydroxide to be added was added, then all of the anhydrous sodium hydroxide to be added was added, and finally, the remaining half of the aqueous sodium hydroxide was added. The anhydrous caustic soda was in the form of 0.7 millimeter diameter, 99 percent anhydrous, prilled pellets.

Thereafter, 400 milliliters of distilled water at 4 to 6 degrees Centigrade was added to the reaction composition, followed by an additional 5 minutes of stirring.

The organic and aqueous phases were then separated. The results for the three Examples are given in Table II.

TABLE II

| | Effect of Substitution of Solid Sodium Hydroxide | | | |
|---|---|---|---|---|
| Example | Aqueous NaOH grams Anhydrous Basis | Solid NaOH grams Anhydrous Basis | Yield | Percent Chloroformate Chloride |
| II | 102.8 grams | 34.5 grams | 91.9 | 0.001 |
| III | 102.8 grams | 34.5 grams | 91.2 | 0.001 |
| IV | 102.5 grams | 34.5 grams | 91.4 | 0.001 |

While the invention has been described and illustrated with reference to certain details and embodiments, the description is not intended to limit the invention, the scope of which is defined in the claims appended hereto.

I claim:

1. In a method of reacting
  (1) a linear diol bis(chloroformate) having the formula:

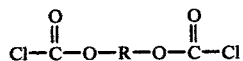

where R is chosen from the group consisting of ethylene, trimethylene, methylethylene, tetramethylene, ethylethylene, pentamethylene, hexamethylene, 2-methylhexamethylene, octamethylene, decamethylene, —CH$_2$—O—CH$_2$—, —CH$_2$CH$_2$—O—CH$_2$CH$_2$—, —CH$_2$—O—CH$_2$CH$_2$—, —CH$_2$CH$_2$CH$_2$—O—CH$_2$CH$_2$CH$_2$—, —CH$_2$CH$_2$—O—CH$_2$CH$_2$—O—CH$_2$CH$_2$—, and —CH$_2$—O—CH$_2$CH$_2$—O—CH$_2$— groups; with
  (2) an allyl alcohol in the presence of sodium hydroxide and water to form the linear diol bis(allyl carbonate) thereof, the improvement comprising feeding aqueous and anhydrous sodium hydroxide to the reaction, where said sodium hydroxide is from 54 to 61 weight percent of the total sodium hydroxide, anhydrous basis, and water initially fed to the reaction.

2. The method of claim 1 wherein the allyl alcohol has the formula:

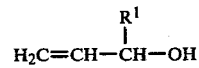

where R$^1$ is chosen from the group consisting of hydrogen, a halogen, and 1 to 4 carbon alkyl group.

* * * * *